United States Patent [19]

Pietzsch et al.

[11] Patent Number: 4,692,943
[45] Date of Patent: Sep. 8, 1987

[54] METHOD OF AND SYSTEM FOR OPTO-ELECTRONIC INSPECTION OF A TWO-DIMENSIONAL PATTERN ON AN OBJECT

[75] Inventors: Ludwig Pietzsch, Karlsruhe; Knud Overlach; Detlef Senger, both of Ettlingen; Walter Breunig, Karlsruhe, all of Fed. Rep. of Germany

[73] Assignee: Dr. Ludwig Pietzsch GmbH, Ettlingen, Fed. Rep. of Germany

[21] Appl. No.: 686,663

[22] Filed: Dec. 27, 1984

[30] Foreign Application Priority Data

Dec. 30, 1983 [DE] Fed. Rep. of Germany ....... 3347645

[51] Int. Cl.⁴ .............................................. G06K 9/00
[52] U.S. Cl. ...................................... 382/8; 356/237; 358/106; 358/107; 382/55
[58] Field of Search ...................... 382/6, 8, 55, 37, 38, 382/62; 356/237; 358/106, 107

[56] References Cited

U.S. PATENT DOCUMENTS

| | | | |
|---|---|---|---|
| 3,339,179 | 8/1967 | Shelton, Jr. et al. | 382/55 |
| 4,090,243 | 5/1978 | Kotera et al. | 364/526 |
| 4,441,207 | 4/1984 | Lougheed et al. | 382/49 |
| 4,481,664 | 11/1984 | Linger et al. | 358/106 |
| 4,506,382 | 3/1985 | Hada et al. | 382/54 |
| 4,532,650 | 7/1985 | Wihl et al. | 382/8 |
| 4,556,317 | 12/1985 | Sandland et al. | 356/237 |

Primary Examiner—Leo H. Boudreau
Assistant Examiner—Jose L. Couso
Attorney, Agent, or Firm—L. Lawton Rogers, III; Joseph M. Killeen

[57] ABSTRACT

In a method of opto-electronic inspection of a two-dimensional pattern on an object, especially a printed board, a micro-inspection is carried out by subjecting line-by-line scanned picture elements in pixel-by-pixel fashion to a sequence of picture operations for inspection of dimensions and spacings, and the respective result is compared with the corresponding scanned pixel. At the same time a macro-inspection is carried out by combining the scanned pixels to frames and by respective reduction thereof to a single characteristic picture information, whereupon a comparison is again performed, but this time with the corresponding picture information of a reference picture. In this way it is possible to perform a quick and fully automatic real-time inspection of two-dimensional patterns, for instance printed boards, both for minute and hardly visible defects and for macro-defects.

9 Claims, 14 Drawing Figures

FIG.9

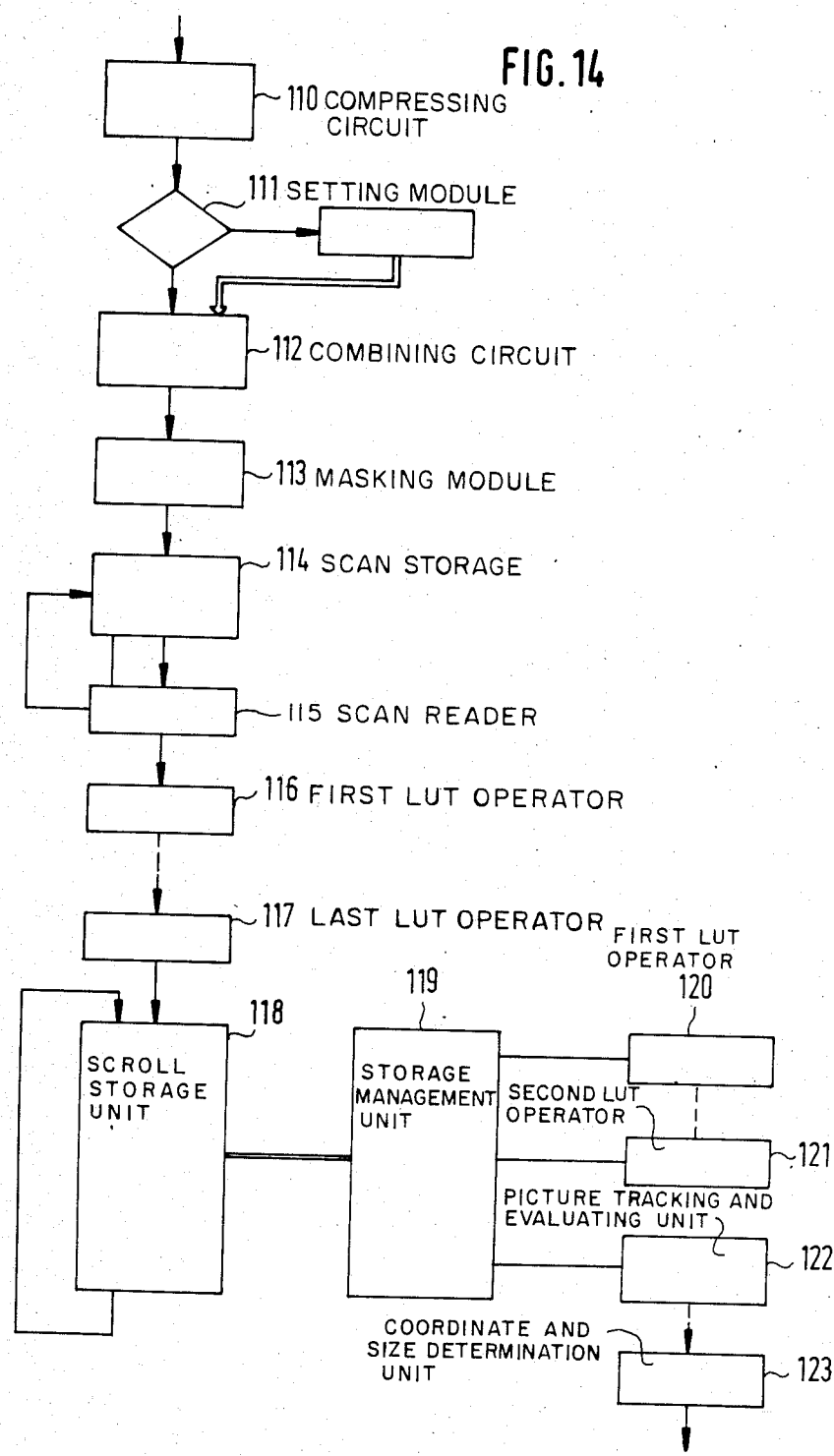

METHOD OF AND SYSTEM FOR OPTO-ELECTRONIC INSPECTION OF A TWO-DIMENSIONAL PATTERN ON AN OBJECT

The invention is directed to a method of opto-electronic inspection of a two-dimensional pattern on an object, especially a printed board, in which the two-dimensional pattern is scanned in line-by-line fashion and the scanned picture elements after processing are compared with corresponding picture elements of a reference picture.

Printed boards have been inspected for defects, deviations or the like substantially visually. In doing so, one must completely rely on the dependability of the inspecting person. It is difficult to visually recognize minute defects, which with increasing packing density of printed circuits or the like on printed boards may well result in failures. Moreover, visual inspection is time-consuming.

With a known opto-electronic inspecting system (DE-OS No. 2,929,846), in which a comparison with a reference board or the like is not performed, the printed boards are inspected on the basis of patterns of specific inspection criteria in an absolute fashion with the aid of an analog signal processing unit and defect detecting circuits connected thereto, the defect indicating outputs of said circuits being taken over by a defect management unit for combination with local coordinates of the path-measuring system of an X-Y-table and storage in a memory until complete passage of the inspected printed board, and which may subsequently be used for moving the printed board such that the defects may be made visible via a display means.

It is the object of the instant invention to provide a method and a system which operate in accordance with the comparison technique and which quickly and reliably detect any defects up to the order of a few microns.

For solving this object it is provided in a method according to the invention that a micro-inspection is performed by subjecting the line-by-line scanned picture elements in pixel-by-pixel fashion to a sequence of picture operations and comparing the respective result with the corresponding scanned pixel as obtained during the scan, and that simultaneously a macro-inspection is performed by combining the scanned pixels to frames and by respectively reducing them to a single picture information characteristic for the respective frame, whereupon each picture information is compared with the charcteristic picture information of the corresponding reference frame and/or is examined on the basis of predetermined geometric criteria.

In a method according to the invention, therefore, a micro-inspection and a macro-inspection are simultaneously performed on a real-time basis, wherein during micro-inspection the processed pixel is compared with the actual pixel and not, as is common practice, with a reference picture that requires a large storage capacity. During micro-inspection it is possible to detect defective spacings and dimensions of minute size down to a few microns. Large-area defects, which are not detected during micro-inspection, will be traced during macro-inspection.

During micro-inspection it is preferred that in the picture operations for micro-inspection, pixel by pixel is either set or cleared in step-by-step fashion in dependence on the surrounding pixels in the two adjacent lines and in the same line.

Advantageously, the characteristic picture information in macro-inspection is obtained by majority vote.

In particular, it is advantageously provided that the picture operations comprise a sequence of dilatations and erosions of each pixel in dependence on the pixels surrounding the same, wherein the sequence "dilatations before erosions" is used for inspecting the spacings between individual conductors or the like and the sequence "erosions before dilatations" is used for inspection of the dimensions of conductors or the like.

Even if the dimensions of the inspected conductor section are correct, a residual picture may be formed during the comparative macro-inspection, said residual picture in accordance with the invention being subjected to a picture cleaning operation, i.e., it will be eliminated when the inspected picture section is correct and it will be classified as a defect when the picture section is not correct.

A system for opto-electronic inspection of a two-dimensional pattern on an object, especially a printed board, comprising a scanning camera for line-by-line scanning of the object, an X-Y-table for supporting the object, said table permitting relative movement of the object with respect to the scanning camera, and a picture processing apparatus in which picture operations are performed for the purpose of defect detection, is characterized in accordance with the invention in that the picture processing apparatus comprises a micro-inspection unit and a macro-inspection unit connected in parallel relationship, output signals from the scanning camera which are converted into digital signals being supplied as inputs to said units.

Preferably, the micro-inspection unit comprises a number of series-connected picture processing units in two groups connected in parallel relationship, each picture processing unit of one group being designed for dilatation and subsequent erosion of each pixel for inspection of the spacings, and each picture processing unit of the second group being designed for erosion and subsequent dilatation for inspection of the dimensions, and further comprises a comparator circuit in which the difference between the processed output signals from the picture processing units and the unchanged scanned picture signals is formed, and finally comprises a picture cleaning unit for processing the differential signals from the comparator circuit.

As regards the apparatus, this concept is implemented in a particularly simple manner in that each picture processing unit includes three pixel environment storages respectively provided for one of three adjacent lines, the first of said storages storing three pixels in a leader line, the second of said storages storing three pixels in a current line, and the third of said storages storing three pixels in a trailer line, and that each pixel environment storage has three outputs connected to a combinatorial storage in which a picture operation "clear" or "set" is executed on the processed pixel in dependence on the eight surrounding pixels. Furthermore each picture processing unit comprises a delay circuit for delaying the scanned unchanged picture signal by a period required for pixel processing.

Advantageously, the invention provides that the second pixel environment storage is preceded by a first line storage for transferring the pixels of one line with a delay of one clock period to the second pixel environment storage, and that the first pixel environment storage is preceded by a second line storage which transfers the pixels of one line with a delay of two clock periods to the first pixel environment storage.

A computer may be provided for overall defect acquisition and management.

Further advantageous configurations of the invention are correspondingly protected by the subclaims.

The invention will be described in detail below with reference to schematic drawings, in which:

FIGS. 9 to 13 show binary pictures in various stages of processing, said pictures being processed by a method according to the invention; and FIG. 14 is a flow chart for a method according to the invention.

The defects occurring with printed boards may generally be classified into micro-defects and macro-defects. Hereinbelow, micro-defects are those whose dimensions are smaller than the minimum acceptable width of printed boards and the minimum spacing therebetween.

Macro-defects are all defects of a size larger than micro-defects. The acceptable dimensions for minimum widths of printed boards and minimum spacings therebetween are within the same order of magnitude, i.e., in practice they are between 50 and 100 $\mu$m.

Figure 1:
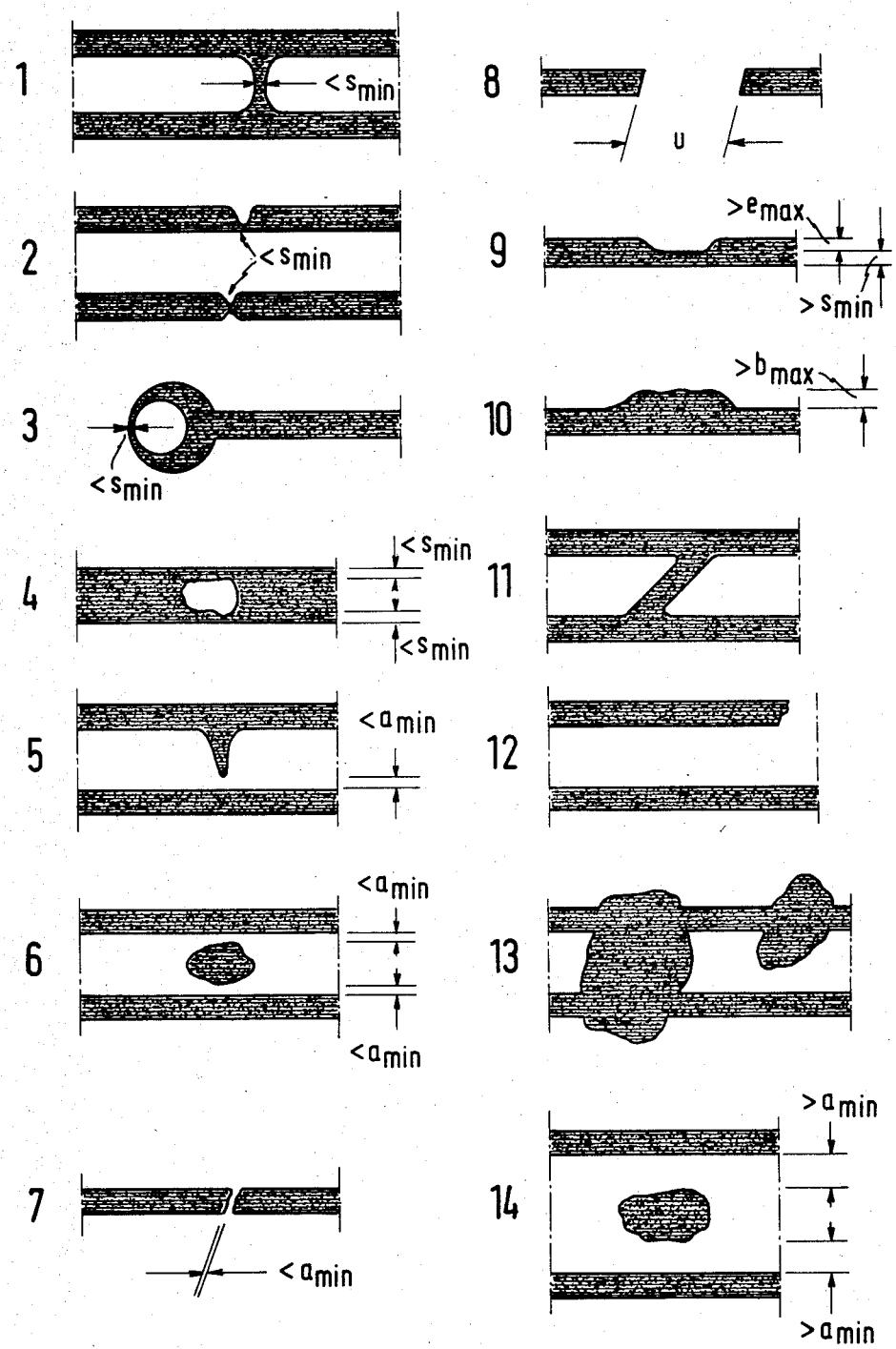
FIG. 1 shows at (1) to (7) typical micro-defects in printed condutors on circuit boards and at (8) to (14) typical macro-defects.

Basically, micro-defects may be distinguished in two groups, viz., one group in which the copper surfaces of the printed boards are too close to each other, i.e., the spacing therebetween is too small, and a second group, in which the copper surfaces become progressively too thin. FIG. 1 (1) to (7) shows typical micro-defects, which are:

FIG. 1 (1) a short-circuit bridge,
FIG. 1 (2) constrictions in printed conductors,
FIG. 1 (3) an offset defect during drilling of a through-connection,
FIG. 1 (4) an inclusion in a printed conductor,
FIG. 1 (5) a protruberance from a printed conductor,
FIG. 1 (6) an inclusion between two printed conductors,
FIG. 1 (7) a hairline crack in a printed conductor.

Macro-defects are basically of the same configuration, but their size is larger than that of micro-defects. FIG. 1 (8) to (14) show typical macro-defects, which are:

FIG. 1 (8) an interruption in a printed conductor,
FIG. 1 (9) a constriction in a printed conductor, wherein the remaining wall thickness is, however, greater than $s_{min}$,
FIG. 1 (10) a widened portion,
FIG. 1 (11) an interconnection or short-circuit bridge of a width in the range of that of the printed conductors, conductor end portion,
FIG. 1 (12) a broken printed conductor end portion,
FIG. 1 (13) large-area imperfections,
FIG. 1 (14) an inclusion which has a spacing of more than $a_{min}$ from the adjacent printed conductors.

The specified minimum dimensions $s_{min}$, $a_{min}$, $e_{max}$, $b_{max}$ are self-evident from a study of FIG. 1 and will not be explained in detail. It is intended that $s_{min}$, $a_{min}$ of 80 $\mu$m and $e_{max}$, $b_{max}$ of 20% shall be detected.

It is intended that all of the defects shown in FIG. 1 shall be detected with the method and the apparatus according to the invention as described hereinbelow within a brief inspection period, i.e., within c.10 to 20 s per printed board with a printed board size of 100 cm$^2$.

Figure 2:
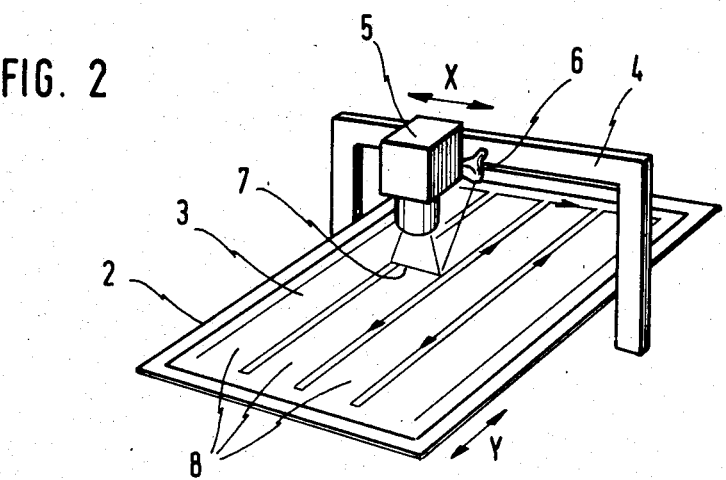
FIG. 2 is a simplified perspective view of an arrangement comprising a camera and an XY-table for supporting a printed board for inspection.

FIG. 2 shows an arrangement including a movable table 2 on which a printed board 3 is supported for inspection. A cross-member 4 mounts a CCD camera (charge coupled device) above the table 2 for movement in X-direction. The table is movable in ±Y-direction on the cross-member 4. It is also possible to employ a usual video camera instead of a CCD camera.

Illuminating means 6 is disposed adjacent the scanning camera 5 for movement with the camera along the cross-member 4. The CCD scanning camera scans a line 7 on the printed board when the latter passes beneath the camera in Y-direction. The time of exposure of the scanning camera is clocked and is not more than 200 $\mu$s with a resolution of 5 to 10 $\mu$ and an advance of the table of 50 mm/s in Y-direction. The CCD camera includes a sensor array with a total of 1024 semiconductor sensors or cells, which are simultaneously exposed during the time of exposure and supply the video signal serially to an output.

The data throughput of each sensor is 10 MHz in pulsed mode for c.100 $\mu$s. On the printed board 3 under inspection, the scanning tracks over which the CCD camera sweeps are indicated at 8, from which it is apparent that an X-movement takes place at the end of each such scanning track.

Instead of moving the table 2 it is also possible to move the cross-member 4 in ±Y-direction. The scanning camera 5 may also be stationary, and the table 2 may be adapted for controlled movement both in X and in Y-direction.

Figure 3:
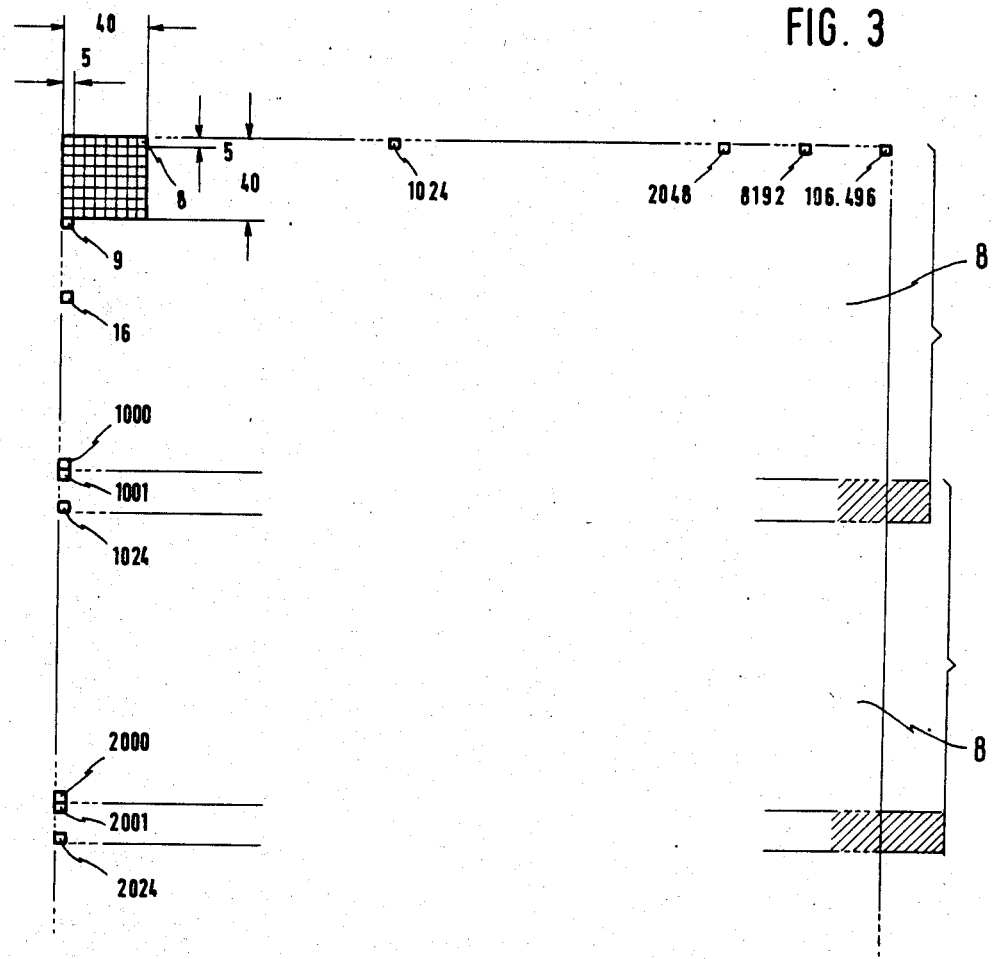
FIG. 3 is a partial view of a printed board to be inspected, showing the dimensions of a picture sector to be subjected to micro-inspection and of the micro-conductors across which the camera shown in FIG. 2 sweeps during the scanning operation.

The fragmentary plan view of the surface of the printed board 3 according to FIG. 3 shows the mode of operation of the scanning arrangement of FIG. 2. In the top left-hand corner of FIG. 3 a frame is shown as being subdivided into 8×8 squares of 5×5 $\mu$m each. One square of 5×5 $\mu$m corresponds to one pixel. The vertical array of 1024 pixels is scanned at an exposure time by the scanning camera 5. The frame comprising the 8×8 squares has a size of 40×40 $\mu$m. Consequently, the width of one micro-path 8 corresponds to 5×1024 squares of a length of 5 $\mu$ each, i.e., 5120 $\mu$m. It is apparent from FIG. 3 that the X-movement of the scanning camera according to FIG. 2 corresponds only to a length of 1,000 squares of pixels, i.e., 5,000 $\mu$m (=5 mm), whence the overlapping of the individual tracks 8 shown in FIG. 3 results. Due to this overlap it is ensured that every part of the printed board is inspected. During the macro-inspection to be described below, the 64 pieces of picture information present in a frame having a length of 40×40 μm as indicated in the top left-hand corner of FIG. 3 are reduced to a single picture information.

Figure 4:
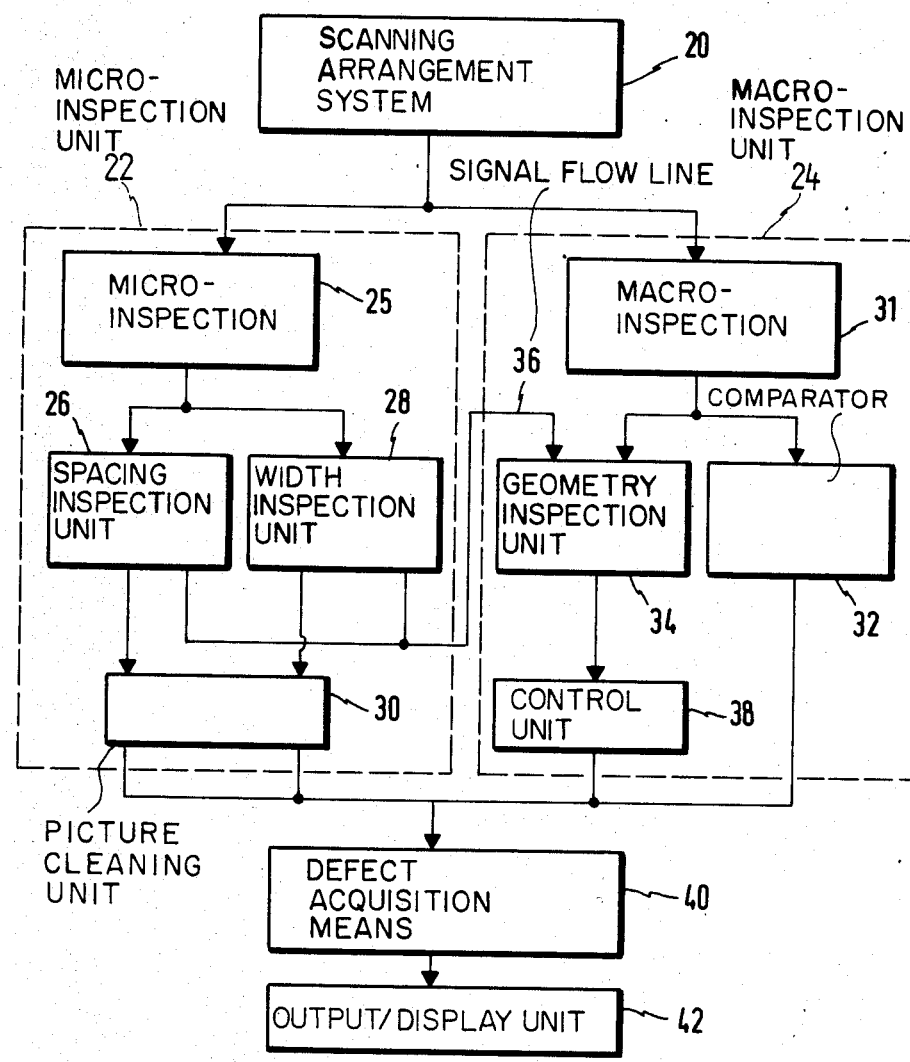
FIG. 4 is a basic diagram of a system according to the invention.

FIG. 4 shows a basic functional diagram of an arrangement for opto-electronic inspection of a printed board or another two-dimensional structure which is provided with a pattern to be inspected.

The scanning arrangement shown in FIG. 2 is indicated in FIG. 4 by a block 20. Picture or video signals picked up with the scanning arrangement 20 are simultaneously supplied to a micro-inspection unit 22 and to a macro-inspection unit 24 outlined in dotted lines in FIG. 4.

In the micro-inspection unit, pixel-by-pixel micro-inspection of the picture elements of a size of 5×5 μm according to FIG. 3 takes place, which is indicated by a block 25. Simultaneously, in a spacing inspection unit 26 and a width inspection unit 28, spacing defects and width or dimensional defects of a size betwen 10 and 100 μm are compared pixel by pixel through differentiation and comparison with corresponding reference pixels. The resulting residual picture is "cleaned" in a picture cleaning unit 30, i.e., it is checked whether it represents a "true" defect or has resulted only from procedural deviations wherein the spacings or widths do not deviate unacceptably from the corresponding desired values.

In the macro-inspection unit 24, the single-picture signal, which is reduced for each 40×40 μm frame, is subjected to macro-inspection as indicated by the block 31. In a comparator 32 direct comparison with corresponding reference picture information is made, whereby information relating to defects in the order of magnitude of greater than 100 μm is obtained. At the same time, the obtained picture information may be selectively subjected to a so-called "geometry inspection" in a geometry inspection unit 34, wherein geometric criteria relating to the shape (e.g. the form of the gradient, the linearity or the like) are utilized for inspecting the correct geometric shape of a printed board. When no reliable information concerning the defect has been obtained in the units 26, 28 of the micro-inspection unit 22, a corresponding signal from the units 26, 28 may be supplied via a signal flow line 36 to the geometry inspection unit 34.

Finally, a control operation is performed in a control unit 38. The final results from the micro-inspection unit 22 and the macro-inspection unit 24 are supplied to a common overall defect acquisition means 40, for instance a computer, with a succeeding output/display unit 42 connected thereto.

Figure 5:
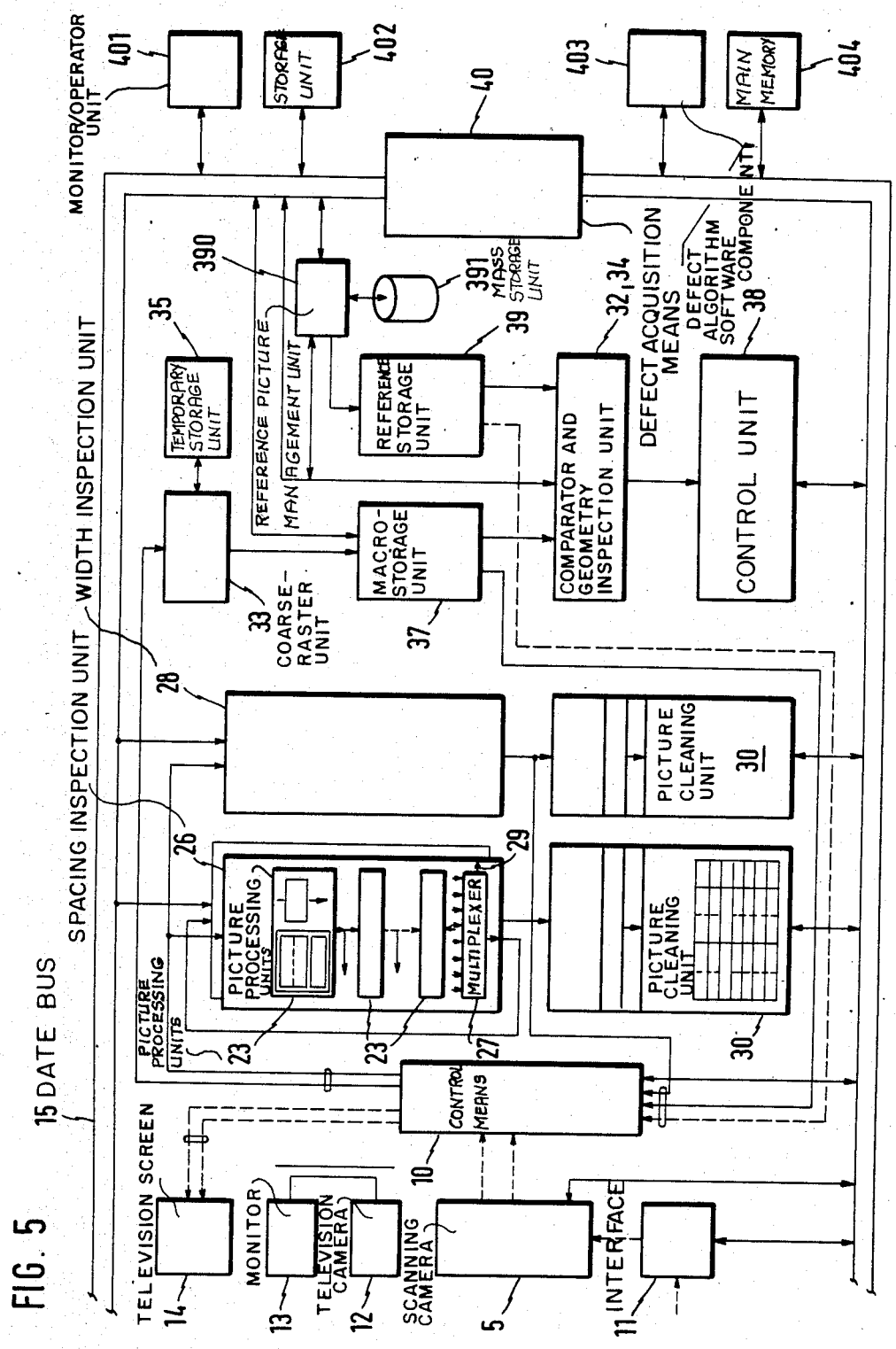
FIG. 5 is a more detailed diagram of the system shown in FIG. 4.

FIG. 5 shows a more detailed diagram than FIG. 4, in which the apparatus concept of a system for opto-electronic inspection of a printed board or another two-dimensional pattern is already indicated.

Basically, the layout of the diagram of FIG. 5 is similar to that of FIG. 4; consequently, the same reference numerals have been used where appropriate.

In the pickup or scanning portion of the system shown on the left-hand side, the CCD camera 5 delivers video control signals and binary video signals to a video bus control means 10 which is connected via digital video busses to the subsequent modules of the micro-inspection unit 22 and the macro-inspection unit 24 as well as the computer 40. The computer is in turn connected into a data bus 15 which is provided to coordinate the processing of defects, marking of defects in the picture, combining of defects, data transfer and operator communication.

Between the movable table and the CCD camera 5 an interface 11 is mounted which like the camera 5 and the video bus control means 10 is connected to the data bus. In addition, a television camera 12 with a monitor 13 may be provided. Moreover, a television screen 14 may be connected to the video bus control means 10.

Figures 6, 7:
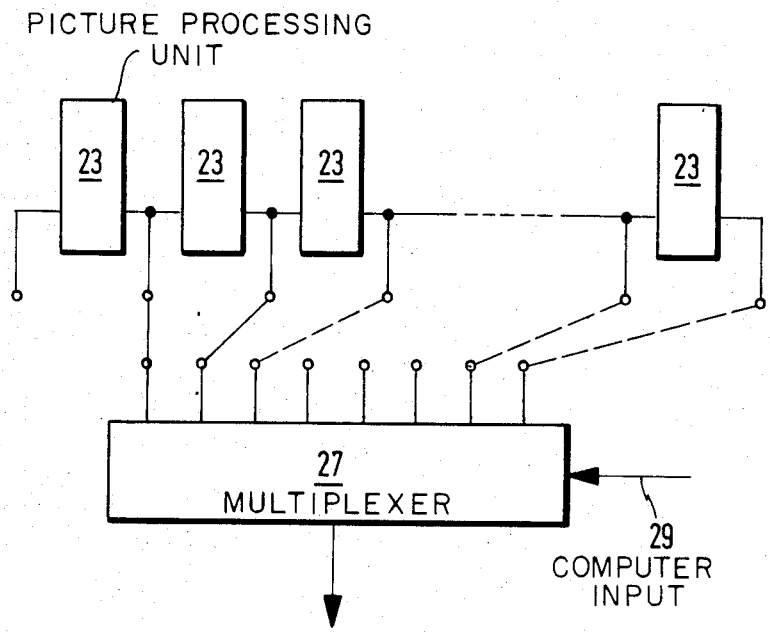
FIG. 6 is a modular circuit representing a detail from FIG. 5.
FIG. 7 is the schematic representation of a picture operation during micro-inspection for processing a pixel with a picture processing unit according to FIG. 6.

The spacing inspection unit 26 and the dimension inspection unit 28 are connected to the video bus control means 10 via digital video busses. Each of the units 26, 28 includes 8 picture processing units 23 which are connected in series and are of identical design in accordance with the following description of FIG. 8. Each picture processing unit supplies an output signal to a multiplexer 27. For the sake of clarity, this is again shown in detail in FIG. 6. Each multiplexer 27 receives an input 29 from the computer 40 through which the selection of picture operations is inputted. From the picture signals received from the picture processing units 23, from the processed picture signals $V_z$, and from the unchanged scanned picture signals $V_{Orig}$ (see FIG. 8), differential picture signals are produced in the multiplexer 27. These differential picture signals are each supplied to an identical picture cleaning unit 30, in which in addition to picture cleaning also picture evaluation, calculation and transfer of the defect coordinates X, Y takes place, as indicated in FIG. 5.

For macro-inspection, the video signals from the video bus control means 10 are supplied to a coarse-raster unit 33 which is interactively coupled to a temporary storage 35 for n−1 scan tracks. The coarse-raster unit is connected to a macro-storage 37 for processing a plurality of scan tracks. A reference storage 39, which is connected to a reference picture management 390 with a mass storage 391 for printed reference boards at the data bus, contains corresponding reference picture information.

For macro-inspection, the output signals from the macro-storage 37 and the reference storage 39 are examined in a module in which the comparator 32 and the geometry inspection unit 34 are combined. A subsequent macro-evaluation unit 38 calculates and transfers defect coordinates to the computer 40.

To the data bus there are additionally connected a monitor/operator unit 401, a setting storage 402 for printed board data such as shapes and tolerances, a software component 403 for defect algorithms, and a main memory 404.

Below, the structure of a processing unit 23 will be explained in detail with reference to FIG. 8. For better understanding, however, it will first be explained with reference to FIG. 7 how a picture processing unit according to FIG. 8 operates.

To each picture processing unit 23 there are successively supplied line-by-line digitalised video signals for a leader line a, a current line b and a trailer line c. A pixel in the current line b is to be processed, viz., the pixel 4b of FIG. 7. All pixels 3a, 4a, 5a in the leader line a which surround said pixel, the pixels 3b, 5b adjacent said pixel in the same line, and the pixels 3c, 4c, 5c in the trailer line are utilized for scanning. The pixel 4b is processed by being subjected to dilatation or erosion. "Dilatation" means that a picture area of a predetermined brightness is dilated by setting the processed pixel to the same brightness provided at least one of its neighbours possesses said brightness. "Erosion" means that a picture area of a predetermined brightness is reduced or contracted by removing (erasing) the processed pixel from said brightness range provided at least one of its neighbours does not have the predetermined brightness.

In the simplest case it will suffice to use exclusively the brightness values "black" and "white", so that binary processing will be sufficient.

When a plurality of such dilatations and a corresponding number of erosions are used in the sequence: dilatations followed by the same number of erosions, a "hole closure effect", i.e., a detection of cracks, fissures, too close spacings and the like, will be obtained. This combination of dilatations, followed by the same number of erosions, is called "fermature". When the sequence: erosions followed by the same number of dilatations is used, a "hole opening effect" is obtained, i.e., a detection of constrictions, too thin printed conductors and the like. Such a sequence is called "overture".

The actual recognition becomes possible only by a comparison of the picture detected in a fermature or overture with the associated original picture. Due to procedural causes, the result of a fermature and of an overture is not necessarily the same even with correct dimensions. In the differential picture, which is produced for comparison purposes and which ought to disappear in case of correct dimensions, remainders will be left. This is the reason why a picture cleaning operation has to be employed for each obtained differential picture. The picture cleaning unit 30 must be able to distinguish between "improper" differential pictures—no defect is present—and "proper" differential pictures. A classification criterion may, for instance, be that the number of pixels in the residual picture in both axial directions contiguously exceeds a predetermined limit value (e.g. greater than two pixels in both axial directions). In this case a proper defect exists.

Below, the structure of a picture processing unit 23, with which a respective picture operation on one pixel may be performed as explained above, will be described in detail.

Figure 8:
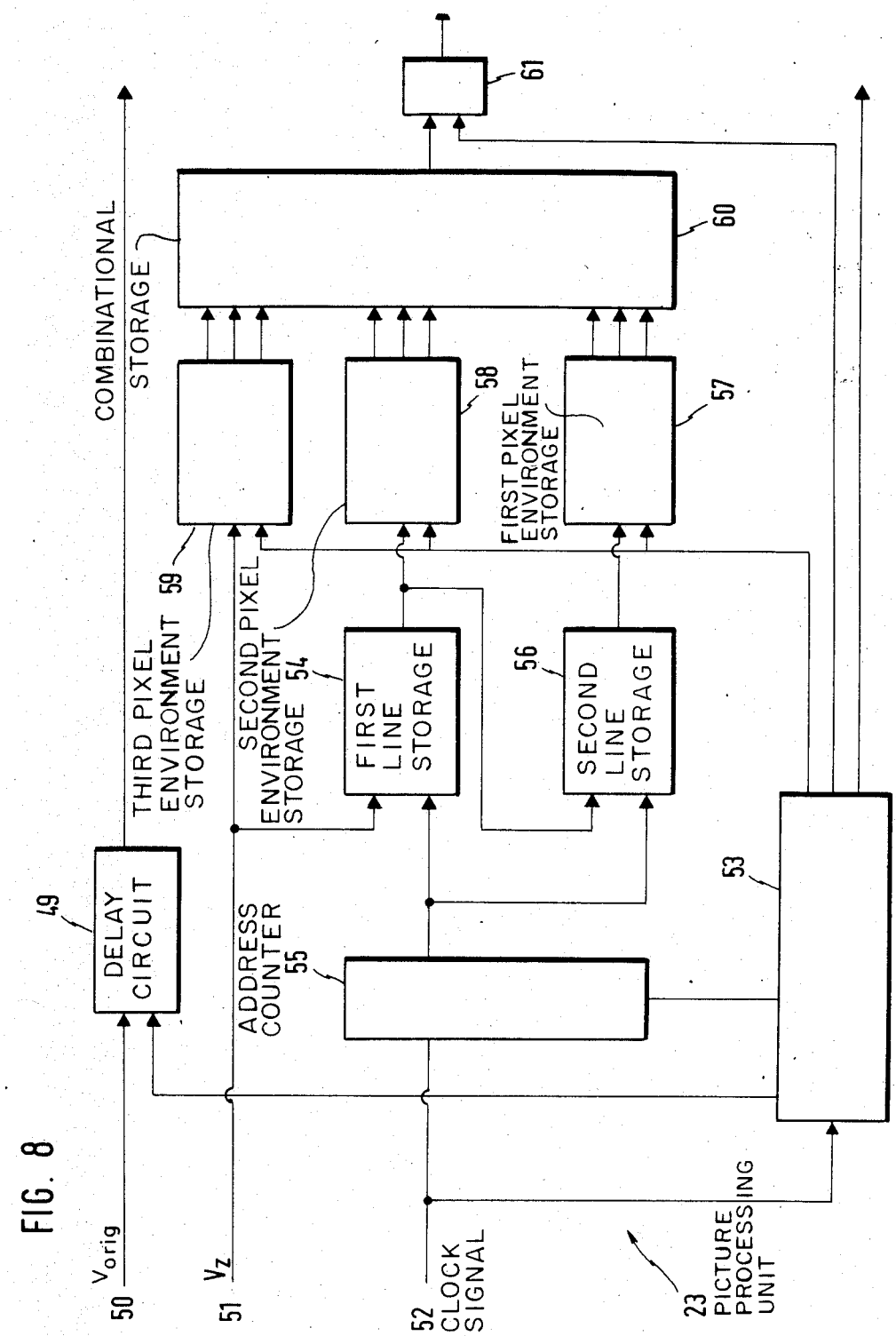
FIG. 8 is the detailed circuit layout of the picture processing system according to FIG. 6.

The picture processing unit 23 of FIG. 8 comprises three inputs 50, 51, 52 for an unchanged digital video signal $V_{Orig}$, a respective video signal $V_z$ to be processed, and a clock signal "Clock", respectively. The video signal $V_{Orig}$ is delayed through a delay circuit 49 in accordance with the processing time of the signal $V_z$. The video signal $V_z$ to be processed is supplied to a first line storage 54. This line storage is driven through a clock address with a delay of one clock by an address counter 55 to which the clock signal 52 is supplied as an input and which counts from 0 to 1023 in accordance with the number of signals per each sensor row of the CCD camera. Thus, the first line storage 54 shifts the picture signals corresponding to one picture line of 1024 pixels after the fashion of a shift register, but delayed by one line clock. The output of the line storage 54 is connected to the input of a second line storage 56, which is also addressed by the address counter 55 and consequently again delays the received picture signals by one line clock, i.e., provides a total of two delays relative to the current values $V_z$. A total of three pixel environment storages 57, 58, 59 are provided. The first pixel environment storage 57 is connected to the second line storage 56 and stores three respective pixel-surrounding pixels of the twice delayed line, i.e., the leader line a. The second pixel environment storage is connected to the first line storage 54 and stores three respective adjacent pixels in the current line b. Finally, the third pixel environment storage 59, which is directly connected to the input 51, i.e., is supplied with the current signal $V_z$, stores three adjacent pixels in the trailer line c.

Each of the three pixel environment storages 57, 58, 59 is connected via three outputs corresponding to the three stored pixels to a combinatorial storage 60, in which the explained picture operation on the central pixel 4b is executed, i.e., a signal is either set or cleared. The resulting output value is transferred to the next-following picture processing unit 23 or, respectively, the multiplexer 27 according to FIG. 6 for further picture processing, i.e., for forming the difference between $V_z$ and $V_{Orig}$.

With the described system it is possible to perform simultaneously in a real-time operation the described micro-inspection (inspection of picture elements of a size of $5 \times 5$ μm) and a macro-inspection (inspection of frames of a size of $40 \times 40$ μm) at relatively high speed. A computer is not absolutely necessary for picture processing; it may be sufficient to supply the results of the macro-inspection and the micro-inspection to an X/Y-coordinate display or a recording means. However, the interconnection to a computer in the described way is reasonable for managing and processing the defects.

If printed boards of different structure are frequently inspected, it will be appropriate respectively to reprogram the mass storage 391 by a teach-in process with picture information of a corresponding non-defective printed reference board.

The method described hereinbelow is used for quick detection, i.e., at the picture sweep frequency or at a pixel frequency of about 10 MHz, of fluctuations in width of any desired structures, normally line-like structures, especially picture structures of the type used on printed conductor boards or printed circuit boards for electronic apparatus.

Basically, the method is composed of three steps, viz.:
(1) processing of the binary picture supplied by the scanning camera 5 (FIG. 2) to form a pseudo grey picture, in which the grey values represent a measure of the distance from the contour of the original binary picture,
(2) reducing the pseudo grey picture to lines of maximum grey value, and
(3) scanning the lines according to step (2) and marking unacceptable grey-value fluctuations.

In this connection the concept of "grey value" or "grey picture" by no means corresponds to any brightness values of the original picture. These terms have been chosen merely because the use of different grey values is one possibility of representing equidistant lines of the binary picture contour on a data display unit.

Figure 9:
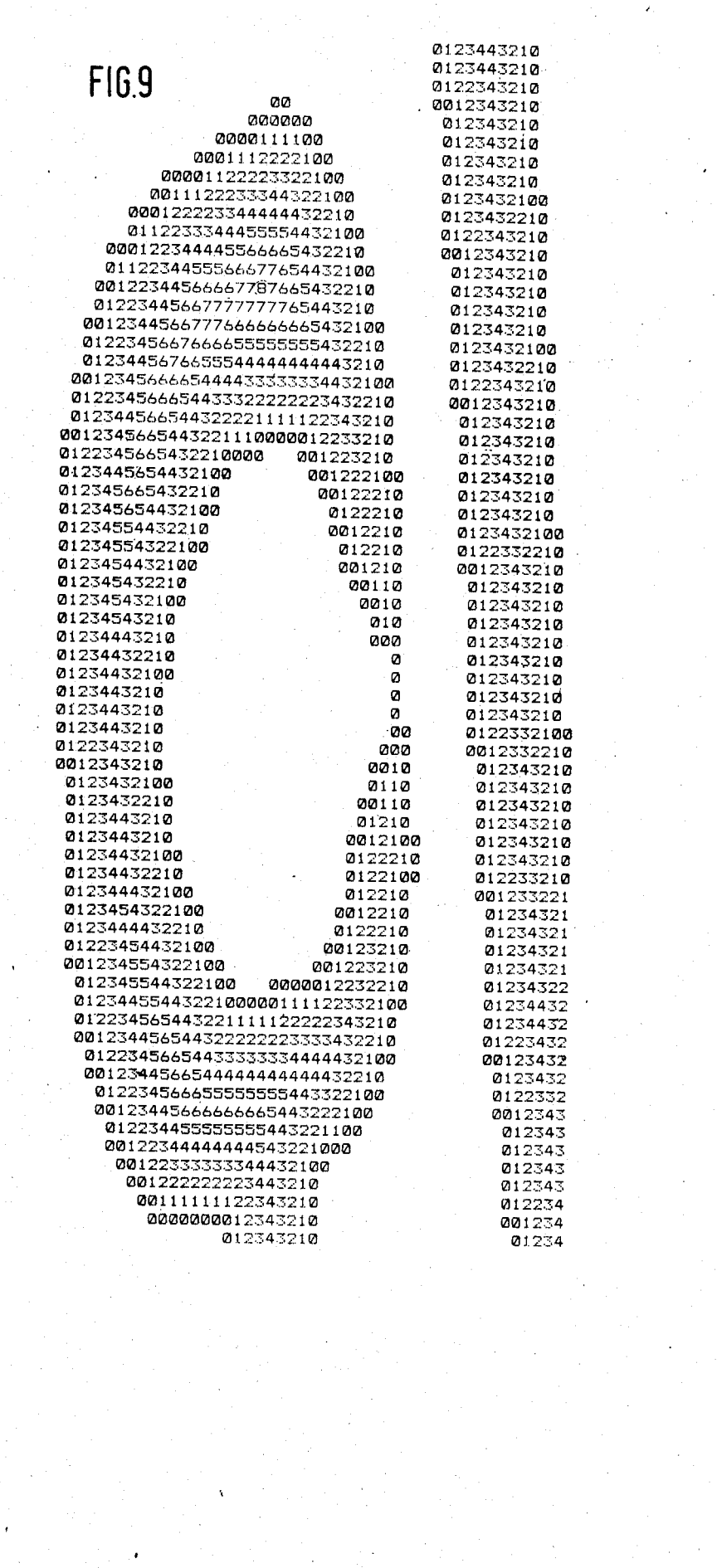

FIG. 9 illustrates what is meant by processing the binary picture according to step (1). Each binary pixel is marked by a number between 0 and 8. The value of the number indicates the distance from the contour, i.e., 0 means "marginal pixel" while 8 marks the greatest existing distance from the margin.

Figure 10:
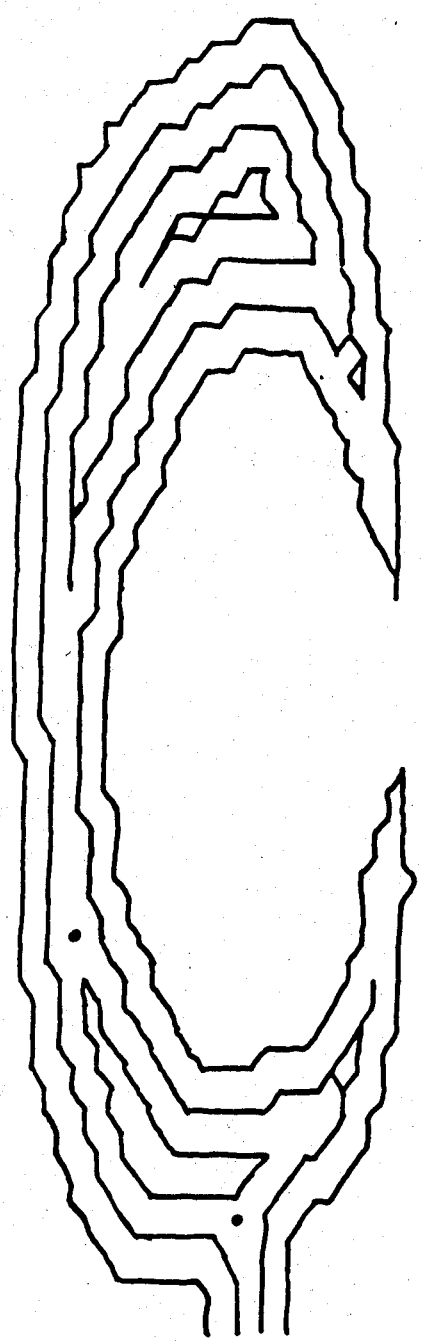

The binary picture is processed in accordance with the following rule:

A certain number of erosions is executed by means of look-up operations (LUT operations). The look-up table for processing is configured so that the resulting pixels are assigned a grey value from which the sequence number of the erosion may be inferred. For instance, at the third erosion the pixels are assigned the grey value 3, at the fourth erosion the grey value 4, etc. Thereby, sequences of pixels of identical grey value are formed in the picture, which sequences after joining with each other result in continuous lines similar to contour lines found in maps. FIG. 10 illustrates for a section of FIG. 9 the contour lines having the grey values 1, 3, 5 and 7. (For clarity's sake the contour lines existing therebetween have not been illustrated.) The grey values of the pixels constitute a measure for the distance of the pixels from the outer contour in terms of pixels. When all erosions have been executed and further unprocessed pixels exist, these are marked with a predetermined grey value which indicates that at this location, for instance, a width inspection is no longer necessary, because this section has the required minimum width. In this connection the width inspection is not limited to the number 8—as in the example of FIG. 9—but may basically be extended as far as desired. In the actual case, however, the operation will be terminated at an appropriate position, e.g. when a predetermined minimum or maximum width has been reached.

Figure 12:
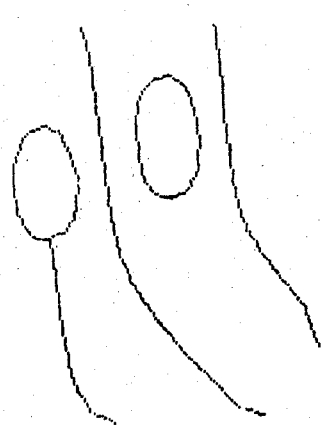

In step (2) the "grey picture" is reduced to its "crest lines". To this end the "contour lines" are sequentially processed from the outside towards the inside. During each run a portion of the pixels of the processed "contour line" is erased, which is of no consequence for the further processing. The result is a single continuous line (FIG. 12). The grey values of the line pixels of the crest line constitute a measure for the distance pixel—outer contour, and that approximately in the direction of the normal from outer contour to pixel.

Figure 11:

FIG. 11 is a binary illustration of the initial picture on which the FIGS. 9 and 10 are based, wherein in this case each pixel is likewise represented by a spot. FIG. 12 shows the "crest line", the grey values of which are now subjected to further processing according to step (3).

In this step, the formed "crest lines" according to FIG. 12 are scanned spot by spot, and any variations of the assigned grey values and thus of the widths of the objects or structures under inspection are examined. A line section extends from a starting spot (open line end) or a branching spot (spot where several lines meet) to a starting spot or to a branching spot. All line sections are examined separately; the connection with other line sections is insignificant. During spot-by-spot scanning of the line the difference of the grey values of two successive spots is respectively formed. When the difference is 0, the line in these spots is designated "continuous". When the difference is other than 0, it is designated "discontinuous". On the basis of the length of continuous or, respectively, discontinuous line sections, the maximum deviation from the initial value, and the cumulated differences, a portion of the line and thus also the associated portion of the object is eventually marked as being defective.

The criteria according to which it is decided whether or not a defective object is concerned may vary from one object under inspection to the next and may have to be fixed in detail in each case. With an appropriate selection of criteria the example of FIG. 11, which is concerned with printed conductors and eyelets, may be processed with the object of detecting unacceptably great fluctuations in the width of the eyelets.

Figure 13:
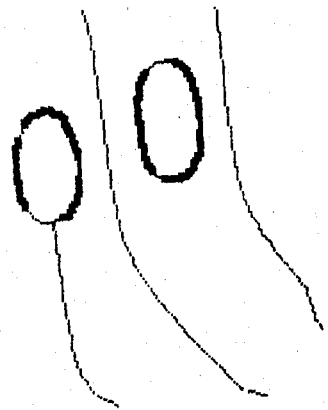

FIG. 13 shows, for example, that the width fluctuations are unacceptable and are therefore marked by a widening of the crest line.

Below, it is explained with reference to the flow chart of FIG. 14 in what way width variations of geometric structures may be detected with the above-described method and a system according to the invention by means of an inventive sequence of binary picture operations.

In a macro-inspection unit according to the macro-inspection unit 24 of FIG. 4 the processed black-and-white picture stream is compressed by the factor K=3—15. This is achieved by initially compressing each scan (cell) by K in a circuit 110 (FIG. 9). From the K pixels a white or black spot is respectively determined in 110 by majority vote. Thereupon scans which are K compressed in this way are combined in 112 and after renewed majority vote are compressed into a single scan.

The overlap between the scans (which is necessary for micro-inspection) is masked out in a module 113.

In a scan storage 114 the compressed scans are combined to form a complete scan. The scan storage 114 comprises two identical areas which alternatively collect the compressed data and, respectively, offer data for further processing. Due to this temporary storage the subsequent LUT-operations become independent of the time slot pattern of the scans and the scanning direction.

After completion of the scan operation the conversion of the binary picture information in a grey picture is started by a first LUT operator 116. In a scan reader 115 the picture information is read out prior to being transferred to the first LUT operator.

With the aid of a sequence of LUT operators the last of which are designated by reference numeral 117 the grey values for ascertaining the "contour lines" according to FIGS. 9 and 10 are determined. The number of grey values (contour lines) depends on the width of the objects subjected to processing, and the number of LUT operators also depends thereon, i.e. after i operators the sequential processing may be abandoned.

The thus produced grey-value picture is stored in a scroll storage 118. Further LUT operators have access to this area via a storage management 119 and reduce the pseudo grey picture to lines of maximum grey values. This processing step requires LUT-operators, the first and the last of which being designated by 120 and 121, respectively The main function of the scroll storage 118 is tracking of the grey-value lines in order to mark unacceptable fluctuations. In order to enable tracking of these lines by means of a picture tracking and evaluating unit 122, the scroll storage 118 should cover a picture sector of maximum possible size.

When the picture marking process is completed, the coordinates and sizes of the marked areas are determined in a module 123 and thereupon are transferred to a host computer for further processing.

We claim:
1. A system for opto-electronic inspection of a two-dimensional pattern on an object, especially a printed board, comprising a scanning camera for line-by-line scanning of the object, an X-Y-table for supporting the object, said table permitting relative movement of the object with respect to the scanning camera, and a picture processing apparatus in which picture operations are performed for the purpose of defect detection, characterized in that the picture processing apparatus comprises a micro-inspection unit (22) and a macro-inspection unit (24) connected in parallel relationship, output signals from the scanning camera (5) which are converted into digital signals being supplied as inputs to said units, further characterized in that the macro- inspection unit (24) comprises a coarse-raster unit (33) in which a picture information "bright" or "dark" characteristic for an entire frame is formed from a plurality of pixels of said frame according to a majority vote, a macro-storage (37) for said picture information, a reference storage (39) for corresponding picture information of the reference picture, a comparator (32) for comparing the characteristic picture information with the reference picture information, and a geometry inspection unit (34) for inspecting the obtained picture information on the basis of predetermined geometric criteria.

2. A system for opto-electronic inspection of a two-dimensional pattern on an object, especially a printed board, comprising a scanning camera for line-by-line scanning of the object, an X-Y-table for supporting the object, said table permitting relative movement of the object with respect to the scanning camera, and a picture processing apparatus in which picture operations are performed for the purpose of defect detection, characterized in that the picture processing apparatus comprises a micro-inspection unit (22) and a macro-inspection unit (24) connected in parallel relationship, output signals from the scanning camera (5) which are converted into digital signals being supplied as inputs to said units, and further characterized in that the micro-inspected unit (22) includes a number of series-connected picture processing units (23) in two groups (26, 28) connected in parallel relationship, each picture processing unit of one of said two groups being designed for dilatation and subsequent erosion of each pixel for inspection of the spacings, and each picture processing unit of the other of said two groups being designed for erosion and subsequent dilatation for inspection of the dimensions, that the micro-inspection unit (22) furthermore includes a comparator circuit (27) in which the difference between output signals processed from the picture processing units (23) and said signals from the scanning camera (5) is formed, and that the micro-inspection unit includes a picture cleaning unit (30) for processing the differential signals from the comparator circuit (27).

3. A system as claimed in claim 2, characterized in that each picture processing unit (23) includes three pixel environment storages (57, 58, 59) respectively provided for one of three adjacent lines, the first (57) of said storages storing three pixels in a leader line (a), the second (58) of said storages storing three pixels in a current line (b), and the third (59) of said storages storing three pixels in a trailer line (c), and that each pixel environment storage has three outputs connected to a combinatorial storage (60) in which a picture operation "clear" or "set" is executed on a processed pixel in dependence on the eight surrounding pixels, and that furthermore a delay circuit (49) is provided for delaying said signals from the scanning camera (5) i.e., one of the signals (V Orig.).

4. A system as claimed in claim 3, characterized in that the second pixel environment storage (58) is preceded by a first line storage (54) for transferring the pixels of one line with a delay of one clock period to the second pixel environment storage (58), and that the first pixel environment storage (57) is preceded by a second line storage (56) which transfers the pixels of one line with a delay of two clock periods to the first pixel environment storage.

5. A system as claimed in claim 2 characterized in that the macro-inspection unit (24) comprises a coarse-raster unit (33) in which a picture information "bright" or "dark" charcteristic for the entire frame is formed from a plurality of pixels of a frame according to a majority vote, a macro-storage (37) for said picture information, a reference storage (39) for corresponding picture information of the frames of the reference picture, a comparator (32) for comparing the characteristic picture information with the reference picture information, and a geometry inspection unit (34) for inspecting the obtained picture information on the basis of predetermined geometric criteria.

6. A system as claimed in claim 5, characterized in that an additional input of the geometry inspection means is formed by an output of the micro-inspection unit (22) by means of which defect signals not fully identified during micro-inspection are delivered.

7. A system as claimed in claim 7 characterized in that the micro-inspection unit (22) and the macro-inspection unit (24) are interconnected with a computer (40) for overall defect acquisition and management.

8. A system as claimed in claim 2 characterized in that the scanning camera is a CCD camera (5).

9. A system for performing the method of opto-electronic inspection of a two-dimensional pattern on an object, especially a printed board, in which the two-dimensional pattern is scanned in line-by-line fashion and the picture elements scanned thereby after processing are compared with corresponding picture elements of a reference picture, characterized in that a micro-inspection is performed by subjecting the line-by-line scanned picture elements in pixel-by-pixel fashion to a sequence of picture operations and comparing the respective results with the corresponding scanned pixels, as obtained during the scan, and that simultaneously a macro-inspection is performed by combining the scanned pixels to frames and by respectively reducing each frame to a single picture information characteristic of the frame, whereupon each picture information is compared with picture information characteristic of a corresponding reference frame and/or is inspected on the basis of predetermined geometric criteria, and characterized further in that a scanned binary picture is processed to form a pseudo grey picture in which the grey values constitute a measure for the shortest distance of the processed picture element to the black/white line of the scanned binary picture, that the pseudo grey picture is reduced to lines of maximum grey values, and that the lines of maximum grey values are tracked and unacceptable grey-value fluctuations are marked, said system characterized in that a macro-inspection unit comprises the following modules:

(a) a module (110) for compressing each scan (cell) by a factor K;
(b) a module (111) for setting the K-pixels obtained in (a) to one of the values "bright" or "dark" according to majority vote;
(c) a module (112) for combining the scans obtained in (b) to a single scan by majority vote;
(d) a module (113) for masking out the overlaps between the scans;
(e) a scan storage (114) for combining the scans according to (c) to form a complete scan;
(f) first LUT operator modules (116, 117);
(g) a succeeding scroll storage (118);
(h) a module (119) for managing and allocating addressess;
(i) succeeding second LUT operators (120, 121);
(k) a module (122) for picture tracking and evaluating; and
(l) a master computer.

* * * * *